(12) United States Patent
Lin et al.

(10) Patent No.: US 9,123,583 B2
(45) Date of Patent: Sep. 1, 2015

(54) OVERLAY ABNORMALITY GATING BY Z DATA

(71) Applicant: Taiwan Semiconductor Manufacturing Co., Ltd., Hsin-Chu (TW)

(72) Inventors: Chun-Hsien Lin, Hsinchu (TW); Kuo-Hung Chao, Hsinchu (TW); Yi-Ping Hsieh, Hsinchu (TW); Yen-Di Tsen, Chung-Ho (TW); Jui-Chun Peng, Hsinchu (TW); Heng-Hsin Liu, New Taipei (TW); Jong-I Mou, Hsinchu (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 112 days.

(21) Appl. No.: 13/940,335

(22) Filed: Jul. 12, 2013

(65) Prior Publication Data

US 2015/0015870 A1 Jan. 15, 2015

(51) Int. Cl.
| | |
|---|---|
| *G01N 21/00* | (2006.01) |
| *H01L 21/66* | (2006.01) |
| *G01N 21/95* | (2006.01) |
| *G03F 7/00* | (2006.01) |
| *G01B 13/06* | (2006.01) |
| *G01B 11/24* | (2006.01) |

(52) U.S. Cl.
CPC ............... *H01L 22/12* (2013.01); *G01B 11/24* (2013.01); *G01B 13/065* (2013.01); *G01N 21/9501* (2013.01); *G03F 7/00* (2013.01); *H01L 22/30* (2013.01); *G01B 2210/56* (2013.01)

(58) Field of Classification Search
USPC ....................................................... 356/72–73
See application file for complete search history.

(56) References Cited

U.S. PATENT DOCUMENTS 7,649,614 B2 * 1/2010 De Mol ........................... 355/77

\* cited by examiner

*Primary Examiner* — Abdullahi Nur
(74) *Attorney, Agent, or Firm* — Eschweiler & Associates, LLC

(57) ABSTRACT

The present disclosure relates to a method of monitoring wafer topography. A position and orientation of a plurality first alignment shapes disposed on a surface of a wafer are measured. Wafer topography as a function of wafer position is modeled by subjecting the wafer to an alignment which simultaneously minimizes misalignment between the wafer and a patterning apparatus and maximizes a focus of radiation on the surface. A non-correctable error is determined as a difference between the modeled wafer topography and a measured wafer topography. A maximum non-correctable error per field is determined for a wafer, and a mean variation in the maximum non-correctable error across each field within each wafer of a lot is determined, both within a layer and across layers. These values are then verified against a set of statistical process control rules to determine if they are within a specification limit of the manufacturing process.

20 Claims, 9 Drawing Sheets

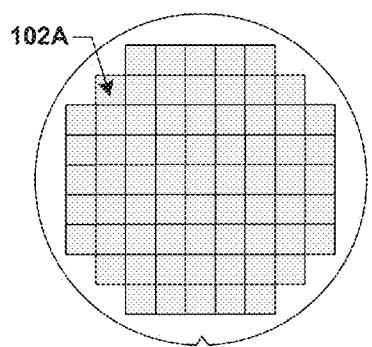
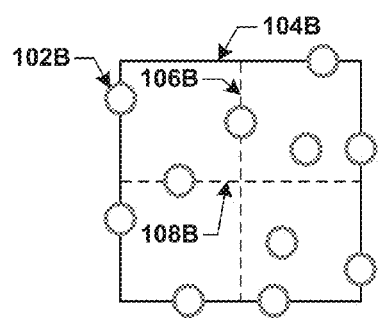
Fig. 1A
Fig. 1B
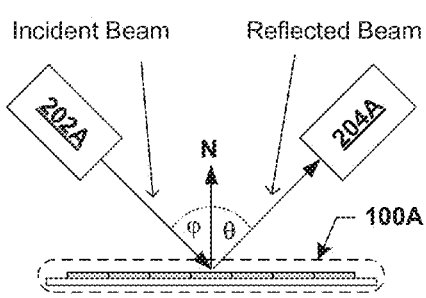
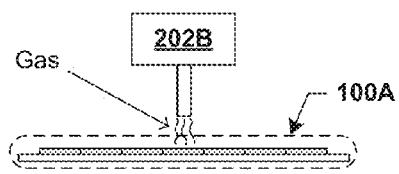
Fig. 2A
Fig. 2B

OVERLAY ABNORMALITY GATING BY Z DATA

BACKGROUND

The following disclosure relates to overlay metrology and methods to achieve enhanced overlay control between two or more alignment events while maintaining manufacturing throughput for semiconductor fabrication process.

BRIEF DESCRIPTION OF THE DRAWINGS

FIGS. 1A-1B illustrate a patterned wafer consisting of a periodic array of reticle fields, where each reticle field contains a configuration of alignment structures.

FIGS. 2A-2B illustrate some embodiments of surface measurement tools configured for wafer topography measurements.

DETAILED DESCRIPTION

Figure 3:
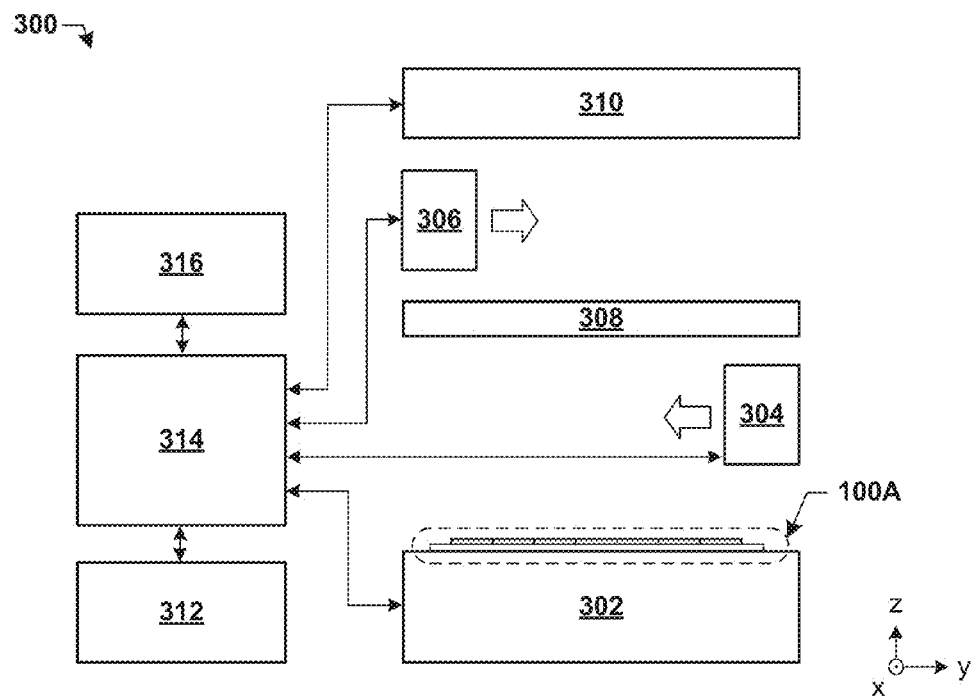
FIG. 3 illustrates some embodiments of a metrology system configured to monitor surface topography of a wafer.

The present disclosure will now be described with reference to the drawings wherein like reference numerals are used to refer to like elements throughout, and wherein the illustrated structures are not necessarily drawn to scale. It will be appreciated that this detailed description and the corresponding figures do not limit the scope of the present disclosure in any way, and that the detailed description and figures merely provide a few examples to illustrate some ways in which the inventive concepts can manifest themselves.

Silicon wafers are manufactured in a sequence of successive lithography steps comprising mask alignment, exposure, photoresist development, layer etch, and layer growth or deposition to form a pattern which defines device structures within an integrated circuit (IC). To facilitate mask alignment, dedicated alignment shapes are placed within physical layout data of the IC, and are utilized by an in-line alignment tool to achieve overlay (OVL) control during mask alignment to a wafer in a manufacturing process. As the number of alignment structure positions which are sampled in-line increases an increasingly accurate depiction of the wafer topography may be achieved, resulting in an increased accuracy in mask alignment. However, higher sampling rates degrade manufacturing throughput within an in-line manufacturing process. In addition, the wafer edge typically contains a higher degree of topographical variation than near the center. As such, sampling of, and alignment to the wafer edge is neglected in many alignment strategies.

Two contributors to OVL variability are wafer distortion and a tool calibration issue. Wafer distortion may result from thermal effects from the manufacturing process which induces wafer warpage. In prior semiconductor technology nodes (e.g., quarter-micron), thermal effect induced warpage was a negligible effect, but now has become a dominant effect in advanced technology nodes such as 22 nanometer and below. OVL variability due to wafer warpage is further degraded by the shift from 300 mm wafers to 450 mm for volume manufacturing as the total wafer warpage will increase due to the larger wafer size, while current technology node scaling dictates a reduction in the overall OVL budget for the manufacturing process. As such, as little as about 10% of alignment shapes are measured to minimize the throughput constraint. While in-line mask correction techniques may be utilized within automated advanced process control (APC) architecture to correct for wafer warpage when aligning a mask to the wafer for an exposure step within the manufacturing process, not all distortion can be accounted for and corrected, particularly within a vicinity of the wafer edge.

Accordingly, some embodiments of the present disclosure relate to a method of monitoring wafer topography. A position and orientation of a plurality first alignment shapes are measured on a surface of a wafer, wherein the wafer comprises a plurality of fields. A modeled wafer topography as a function of wafer position is defined by subjecting the wafer to a set of symmetry operations comprising translation or rotation about orthogonal axes which minimizes misalignment between the wafer and a patterning apparatus and maximizes a focus of radiation on the surface. A non-correctable error (NCE) is determined as a difference between the modeled wafer topography and a measured wafer topography. A maximum NCE per field is determined for a wafer, and a mean variation in the maximum NCE across each field within each wafer of a lot comprising a plurality of wafers is determined, both within a layer and across layers. These values are then verified against a set of statistical process control (SPC) rules to determine if they are within a specification limit of the manufacturing process.

FIG. 1A illustrates a patterned wafer 100A (e.g., Si or SOD consisting of a periodic array of fields 102A. In some embodiments, each field 102A contains an IC which is patterned by a step-and-repeat tool configured align a patterned mask to an individual field 102A based upon a wafer map of alignment structure locations obtained from physical layout data of the IC. In some embodiments, the physical layout data of the IC comprises a GL1, OASIS, or GDSII format, is created in a CADENCE VIRTUOSO or MENTOR GRAPHICS design window, and is assembled into the into a wafer-level periodic array of fields 102A comprising one or more alignment shapes within each field 102A.

FIG. 1B illustrates the field 102A containing a configuration of alignment shapes 102B formed on one or more layers on a surface of the wafer. In some embodiments, the one or more layers comprise gate poly silicon, oxide definition shapes for source/drain formation, local interconnect shapes, via and contact shapes, and metallization shapes among others. In some embodiments, the locations of the alignment shapes 102B are chosen to coincide with a boundary 104B of the field 102A, a first orthogonal centerline 106B, or a second orthogonal centerline 108B. In some embodiments, the field 102A contains additional metrology structures for additional OVL control during a mask alignment event, to monitor critical dimension (CD) variation and across-chip variation of layout topologies across a plurality of fields 102A disposed on a surface of the wafer 100A, etc.

During mask alignment, a scanning tool measures the location of an alignment shape 102B within a field 102A disposed on a surface of the wafer 100A and reports displacement of the alignment shape 102B within a plane of the wafer 100A. Below a threshold value the warpage can be accounted for by through an APC architecture by aligning the wafer 100A relative to the exposure tool or adjusting the focus of the radiation passed through the mask to the wafer 100A. Above the threshold the warpage cannot be accounted for by the APC architecture. The scanner will determine the amount of residual deformation that can't be compensated by measuring a magnitude and direction for a plurality of residual alignment vectors formed between a plurality of first alignment shapes formed on a surface of the wafer and a plurality of second alignment shapes formed on the mask after the alignment and focus adjustment. A mean +3 sigma value for the residual vectors is determined along with a distribution of the residual vectors to achieve a residual overlay performance indicator (ROPI) of the alignment. After alignment, cosine similarity is measured between the residual vectors both across lot and across wafer (within a lot) for comparison.

The ROPI and cosine similarity measure both wafer deformation and alignment performance. However, they do not provide the actual topography of the wafer. FIG. 2A illustrates some embodiments of an optical measurement tool 200A configured to measure the surface topography of the wafer 100A. The optical measurement tool 200A comprises an emitter 202A configured to emit a focused incident beam of radiation to the surface of the wafer 100A at a first angle $\phi$ with a normal vector N to the surface of the wafer 100A. The incident beam is reflected off the surface of the wafer 100A at a second angle $\theta$ to N, and is received by a collector 204A. The optical measurement tool 200A is configured to determine a height of the wafer surface as a function of position from the incident and reflected beams of radiation to provide a measured wafer topography $Z_{MAP}(x,y)$. In some embodiments, the optical measurement tool 200A is configured to determine $Z_{MAP}(x,y)$ from the first angle $\phi$ or the second angle $\theta$ with a resolution that is greater than a resolution of the alignment structure location spacing.

FIG. 2B illustrates some embodiments of a physical measurement tool 200B configured to measure the surface topography of the wafer 100A. In some embodiments, the physical measurement tool 200B comprises an Air Gauge Improved LEveling (AGILE) tool. In some embodiments, the physical measurement tool 200B comprises an air gauge 202B configured to discharge a gas locally onto a surface of a wafer 100A, and to detect a variation in a pressure of the gas as a function of position within a plane of the wafer 100A, and to determine a height of the surface of the wafer 100A as a function of the variation in pressure. The physical measurement tool 200B is further configured to define $Z_{MAP}(x,y)$.

The optical measurement tool 200A and the physical measurement tool 200B do not utilize or recognize alignment structures, and measure the surface topography of the wafer 100A with a resolution that is greater than a resolution of the alignment structure location spacing. In some embodiments, the optical measurement tool 200A and the physical measurement tool 200B are utilized in combination to define $Z_{MAP}(x,y)$. In some embodiments, the optical measurement tool 200A and the physical measurement tool 200B have a resolution of greater than 20,000 points per wafer.

FIG. 3 illustrates some embodiments of a metrology system 300 configured to monitor surface topography of the wafer 100A. The metrology system 300 comprises an alignment stage 302 configured to position the wafer 100A relative to an exposure tool 310 by subjecting the wafer 100A to a set of symmetry operations comprising translation or rotation about orthogonal axes (x,y,z). The exposure tool 310 is configured to provide electromagnetic radiation to the wafer 100A which is filtered by a patterning apparatus 308 (e.g., a quartz photomask). The patterning apparatus 308 contains a pattern defined by opaque areas and transparent areas, where electromagnetic radiation passes through the transparent areas to form a pattern of developed photoresist on a surface of the wafer 100A.

The metrology system 300 further comprises a surface measurement tool 304 configured create a measured topographical wafer map as a function of wafer position $Z_{MAP}(x,y)$. In some embodiments, the surface measurement tool 304 comprises the optical measurement tool 200A, the physical measurement tool 200B, or a combination of the two.

Figure 4:
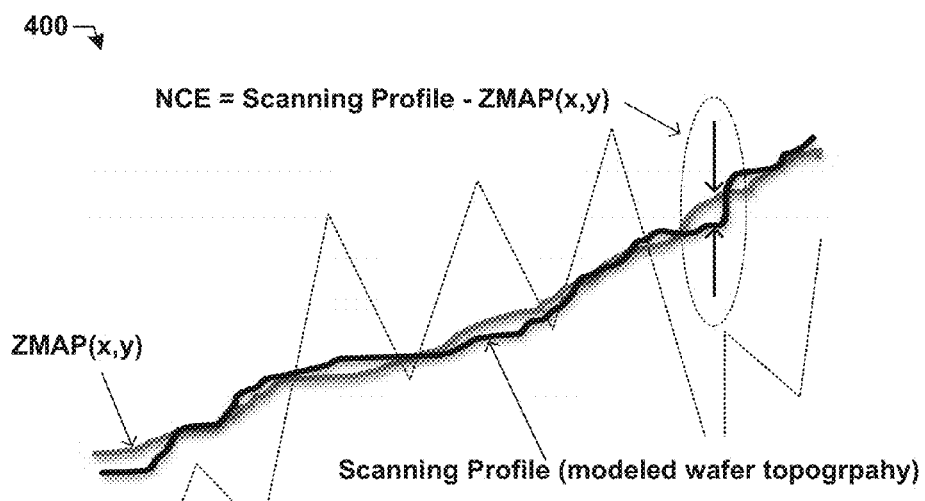
FIG. 4 illustrates some embodiments of a surface topography measurement.

The metrology system 300 further comprises a scanning tool 306 configured to determine locations of a plurality of second alignment shapes formed on a patterning apparatus 308 relative first locations of a plurality of first alignment shapes disposed on a surface of the wafer 100A, and to direct a controller 314 to position the alignment stage 302 based upon the first and second locations. A computation unit 312 is configured to create a modeled wafer map based upon the set of symmetry operations as a function of wafer position, and to determine an NCE as a difference between a modeled wafer map and $Z_{MAP}(x,y)$, as illustrated in the embodiments of the surface topography measurement of FIG. 4.

In some embodiments of the metrology system 300, the computation unit 312 is further configured to determine a maximum NCE error for each field of a wafer, and determine a distribution, standard deviation, and mean variation in the maximum NCE error for each wafer of a lot comprising a plurality of wafers. In some embodiments, the computation unit 312 is further configured to perform a cross-layer comparison between a first NCE of a first layer disposed on wafer surface and a second NCE for a second layer disposed over the first layer to detect topographical variation introduced after disposition of the first layer, or during disposition of the second layer. In some embodiments, the computation unit 312 is further configured to determine that a wafer is unacceptable for a manufacturing process (i.e., "abnormal") if the maximum NCE, the mean variation, or the cross-layer comparison is not within one or more ranges or less than one or more thresholds predetermined for the manufacturing process (i.e., the specification limit of the manufacturing process as enforced through SPC rules).

In some embodiments of the metrology system 300 includes an APC architecture 316 configured to solve multi-variable algorithms to tune a set of inter-dependent process parameters including the position of the alignment stage 302 and focus or dose of the exposure tool 310 based upon the values of the maximum NCE, the mean variation, or the cross-layer comparison. These algorithms are solved by the APC architecture 316 and communicated to the alignment stage 302 and the exposure tool 310 by the controller 314. In some embodiments, the APC architecture 316 within metrology system 300 limits the range of process tuning to a fraction of the complete tool tuning range.

Figure 5:
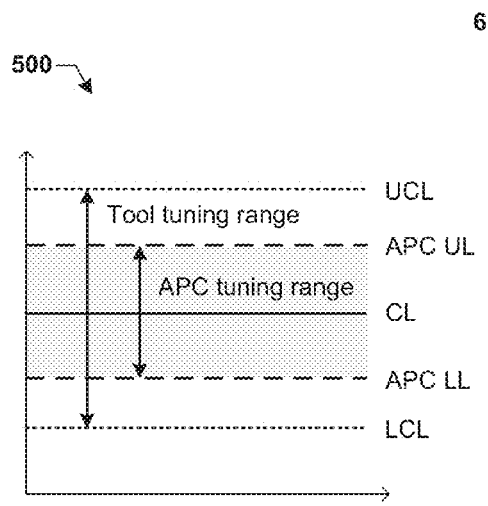
FIG. 5 illustrates some embodiments of a control chart containing an exemplary tuning range for an advanced process control (APC) architecture.

FIG. 5 illustrates a graph 500 of an exemplary APC tuning range within the metrology system 300. The tool tuning range is defined as a first range between a lower control limit (LCL) and an upper control limit (UCL) of the processing tool. In some embodiments, the LCL and UCL comprise lower and upper limits on a symmetry operation of the alignment stage 302 based upon an NCE result (e.g., maximum rotation about an axis, maximum lateral movement along the axis, etc.). In some embodiments, the LCL and UCL comprise lower and upper limits on a patterning operation of the exposure tool 310 based upon an NCE result (e.g., maximum depth of focus or dose, etc.). The exemplary APC tuning range only spans a fraction of the tool tuning range to minimize any degradation to manufacturing throughput resulting from the processing tuning relative to the process target. The APC tuning range is centered around the process target or centerline (CL) value and spans a second range between an APC lower level (LL) and an APC upper level (UL) within the metrology system 300. When a manufacturing outcome deviates from the process target by an amount which exceeds an APC tuning range, the metrology system 300 parameters may have been biased from their tool baseline configuration, and manual tuning of the metrology system 300 parameters may be required. As a result, the metrology system 300 may be taken offline for manual calibration, which can reduce manufacturing throughput while the metrology system 300 is down.

Figure 6A:
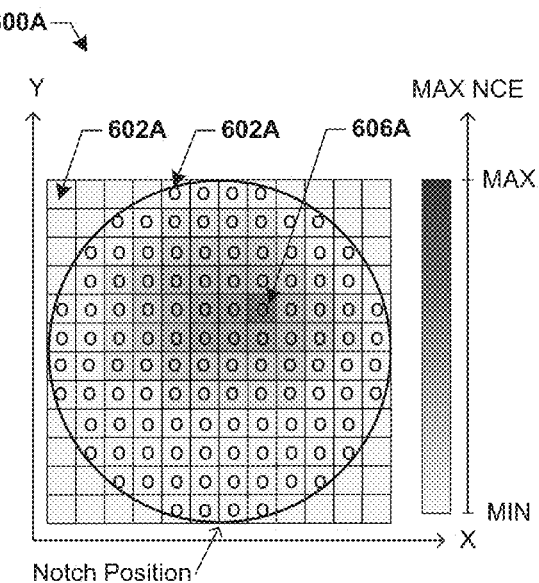
FIGS. 6A-6C illustrate a comparison of some embodiments of a non-correctable error (NCE) measurement with a residual order performance index (ROPI) measurement.
Figure 6B:
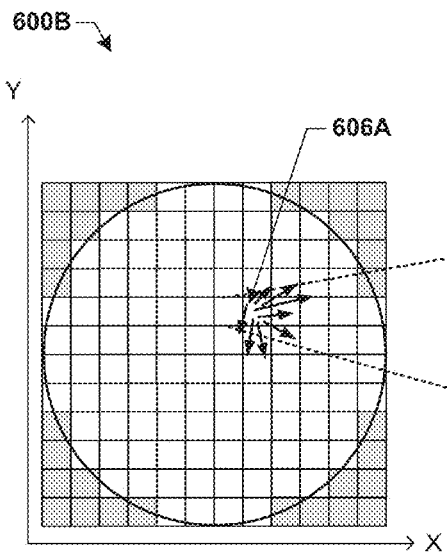
Figure 6C:
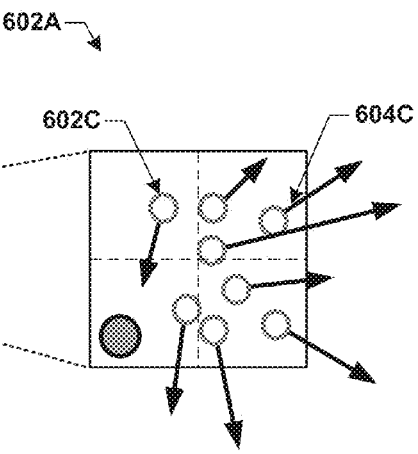

FIGS. 6A-6C illustrate a comparison of some embodiments of a non-correctable error (NCE) measurement with a residual order performance index (ROPI) measurement. One of ordinary skill in the art overlay metrology may recognize that the surface topography $Z(x,y)$ of a wafer is correlated to an average overlay deviation between a plurality of first and second OVL shapes such that increasing a variation in $Z(x,y)$ increases OVL variation, and hence increases the ROPI value. The Z axis variation results in variation in all directions within the plane of the wafer of the alignment stage from a mechanical stage control perspective. Therefore, $Z(x,y)$ is also correlated with a dynamic error of the alignment stage, which introduces error into the modeled wafer map derived from the scanning profile and hence the NCE. If the wafer is not flat the dynamic error or machine offset will increase.

FIG. 6A illustrates a first field map 600A of the wafer 100A, wherein fields 602A within a perimeter 604A of the wafer are "occupied" (denoted by "o") with active layout features and alignment shapes. The first field map 600A includes a two-dimensional (2D) map of the wafer 100A, wherein a maximum NCE value for each field 602A is represented by a degree of shade of the field 602A. A maximum error field 606A is shown to have the largest maximum NCE on the wafer. The maximum NCE is determined as a difference between a scanning profile and a measured wafer topography across the surface of the wafer.

In some embodiments, the measured wafer topography is determined by discharging a gas locally onto the wafer surface, monitoring a variation in a pressure of the gas as a function of position on a surface of the wafer, and determining a height of the wafer surface as a function of the pressure in an AGILE tool. In some embodiments, the measured wafer topography is determined by emitting a focused incident beam of radiation to the wafer surface from a LASER at a first angle with a normal vector to the wafer surface, and reflecting the incident beam of radiation off the wafer surface, resulting in a reflected beam of radiation at a second angle with the normal vector to the wafer surface. A height of the wafer surface as a function of position from the incident beam, reflected beam, first angle, second angle, or other distortion of the incident beam by the wafer surface. In some embodiments, the measured wafer topography is determined by a combination of AGILE and LASER measurements to create a $Z_{MAP}(x,y)$.

FIG. 6B illustrates a second field map of the wafer, where the maximum error field 606A is shown. An exploded view of the maximum error field 606A is shown in FIG. 6C, and includes first alignment shapes 602C. A residual vector 604C for each alignment shape 602C is shown after patterning. During patterning, a scanning tool measures the location of the first alignment shape 602C within a field 602A disposed on a surface of the wafer and reports displacement of the first alignment shape 602C within the x/y plane of the wafer relative to a second alignment shape formed on a patterning apparatus. In some embodiments, the scanning tool will auto compensate for misalignment by using a low order model: adjusting image magnification and location to compensate for deformation. In some embodiments, a scanning profile is determined by aligning a first subset of the plurality of first alignment shapes 602C residing within a field 602A with second subset of a plurality of second alignment shapes formed on a patterning apparatus which aligns to the first subset by subjecting the wafer to a set of symmetry operations which minimizes aggregate misalignment between the first and second subsets within a plane of the wafer. The scanning profile is defined from the set of symmetry operations as a function of wafer position. After alignment, the ROPI may be determined from the residual vectors 604C.

A field sampling rate of between about 10% and about 70% results in less than about 100 measured first alignment shape locations across the wafer (i.e., a resolution of less than 100 points per wafer). This course representation of the wafer topography results in a field resolution of about 1 point per field. In contrast, the $Z_{MAP}(x,y)$ has a resolution of greater than 20,000 points per wafer, or about 300 points per field and a field sampling rate of 100%. Thus, the $Z_{MAP}(x,y)$ can provide a much finer resolution per field than alignment shape sampling. For the maximum error field 606A the largest maximum NCE on the wafer resulting from within-field topographical variation may go undetected if the first alignment shape 602C is not placed in a vicinity of the topography which produces the maximum NCE.

Figures 7, 8:
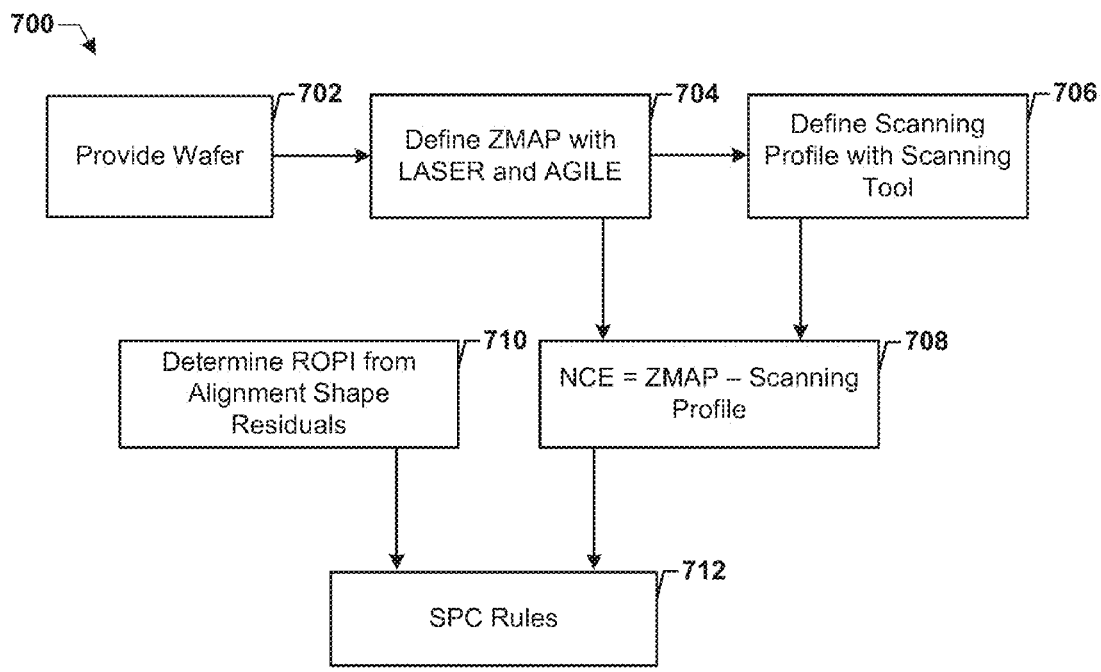
FIG. 7 illustrates a flow chart of some embodiments of an NCE measurement and ROPI measurement for statistical process control (SPC) rules analysis.
FIG. 8 illustrates a table comprising some embodiments of symmetry models within an APC architecture.

FIG. 7 illustrates a flow chart 700 of some embodiments of an NCE measurement and ROPI measurement for statistical process control (SPC) rules analysis. At wafer provided at 702 is subjected to a physical tool measurement (e.g., an air gauge measurement) and an optical tool measurement to produce a $Z_{MAP}(x,y)$ at 704. The wafer is then aligned and patterned with a scanning tool to produce a scanning profile at 706. The NCE is determined as a difference between the $Z_{MAP}(x,y)$ and the scanning profile at 708. Residual deformation that can't be compensated by a symmetry model utilized in alignment and patterning through APC is determined as a sum of mean of the residual vectors and a 3-sigma value of the distribution of residual vectors to get a ROPI. The NCE and ROPI are checked by a set of SPC rules to determine if they are within a specification limit of the manufacturing process at 710.

FIG. 8 illustrates a table 800 comprising some embodiments of symmetry models within an APC architecture. For the embodiments of FIG. 8, the symmetry models are defined as a function of manufacturing layer. For an oxide definition (OD) layer defining source and drain region on a surface of a wafer, no symmetry models are used. For all layers patterned after OD, a single-order correction (SOC) is employed which is a linear correction to the orientation of the wafer, wherein the entire wafer is subjected to a rotation or translation about an orthogonal axis. SOC comprises only a single correction form all fields on a surface of the wafer for a given layer. For a poly-silicon (PO) gate layer formed over OD, a contact (CO) layer formed to make connections to the gate and source/drain regions, and a first metallization (ME1) layer, a correction per exposure (CPE) is utilized, wherein the wafer is aligned individually for each field. CPE utilizes one linear correction term for each field for a given layer resulting from individual alignment measurements within each field. For layers formed after ME1, the CPE correction form each field is fed-forward to the subsequent layers such that the same per field correction is utilized for each field for the remaining back end of line (BEOL) layers. For critical front end of line (FEOL) layers PO and CO, an intra-field high-order process correction (iHOPC) symmetry model is used which performs a non-linear correction per field.

Figure 9:
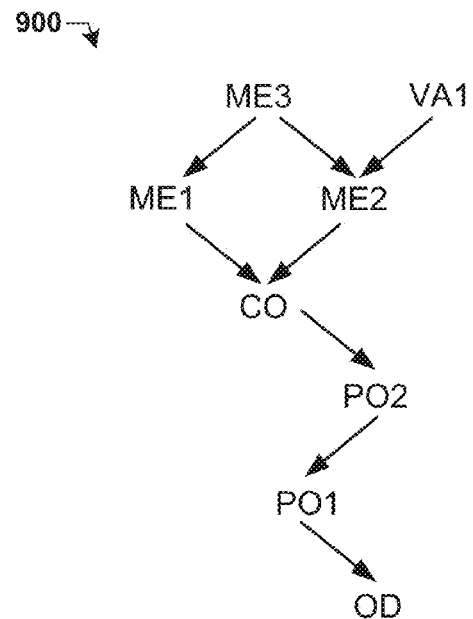
FIG. 9 illustrates some embodiments of an overlay (OVL) tree within a mask alignment sequence.

FIG. 9 illustrates some embodiments of an overlay (OVL) tree 900 within a mask alignment sequence. The OVL tree 900 shows how various masks are aligned to one another while patterning layers within a semiconductor device, wherein a first poly-silicon gate layer (PO1) aligns to an OD layer (i.e., each layer contains corresponding alignment shapes). A second poly-silicon gate layer (PO2) aligns to the PO1 layer. The CO layer aligns to the PO2 layer. First and second metallization layers ME1, ME2 corresponding to a DP metallization process each align to the CO layer. A first via (VA1) layer aligns to the ME2 layer. A third metallization layer ME3 is aligned to a combination of the ME1 and ME2 layers, wherein the alignment is weighted equally between the two layers (i.e., 50% aligned to ME1 and 50% aligned to ME2).

Figure 10:
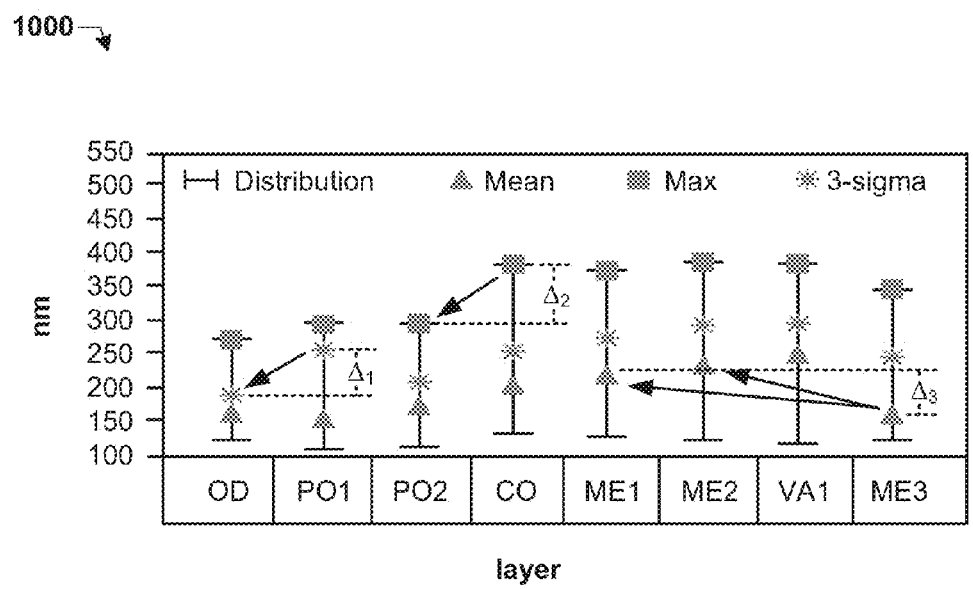
FIG. 10 illustrates a graph of some embodiments of a statistical summary of NCEs by field or by wafer.

FIG. 10 illustrates a graph 1000 of some embodiments of a statistical summary of NCEs by wafer. For the embodiments of FIG. 10, the statistical summary comprises a maximum NCE per field within a wafer for the layers of the embodiments of FIG. 9. Other embodiments comprising a grouping of mean NCE by wafer within a lot, or by in-line tool. For the embodiments of FIG. 10, a scanning profile is obtained by combining an estimation of wafer topography by the scanning tool and focus variation by the exposure tool. The NCE is derived from a difference between the measured surface topography (e.g., by AGILE, LASER, or a combination thereof) and the scanning profile (i.e., modeled topography), and represents the topography that can't be compensated by the scanning tool. The measured surface topography has a resolution of greater than about 20,000 points per wafer. The maximum NCE per field may then be obtained and grouped by layer or by in-line location and verified against a set of SPC rules to define abnormal wafers.

Some embodiments of SPC rules include defining a wafer as abnormal (1) if the maximum NCE within one or more fields to a first threshold, (2) mean variation within a wafer is above a second threshold, or (3) if a cross-layer comparison between maximum NCEs or mean variations is greater than a third threshold. Other SPC rules may also be employed.

For the embodiments of FIG. 10, a first SPC rule includes discarding the wafer or re-disposing a layer if the 3-sigma NCE value varies by greater than a first threshold ($\Delta_1$) of greater than about 80 nm within the layer. A second SPC rule includes discarding the wafer or re-disposing a layer if the maximum NCE value varies by greater than a second threshold ($\Delta_2$) of greater than about 100 nm between the layer and an adjacent layer. A third SPC rule includes discarding the wafer or re-disposing a layer if the mean variation varies by greater than a third threshold ($\Delta_3$) of greater than about 60 nm between the layer and an adjacent layer. Application of these rules to the layers of the embodiments of FIG. 9 drives PO1 layer rework due to a 3-sigma NCE value change between the OD layer and the PO1 layer of greater than A. A CO layer re-disposal also results from a maximum NCE value change between the PO2 layer and the CO layer of greater than $\Delta_2$. A third metallization (ME3) layer rework results from a mean variation between ME3 and an average of ME1 and ME2 greater than $\Delta_3$, because ME3 is 50% aligned to ME1 and 50% aligned to ME2 in the OVL tree 900. The SPC rules of the embodiments of FIG. 10 are applied in accordance with the alignment tree of FIG. 9, wherein a second alignment shape formed on the second layer of an SPC rule is aligned to a first alignment shape formed on the first layer of the SPC rule in the OVL tree 900.

For the embodiments of FIG. 10, the first through third thresholds $\Delta_1$-$\Delta_3$ are within an APC tuning range of a metrology system such that a lot-based APC correction may be applied, wherein a single correction is applied for each lot. If outliers within the distribution (e.g., values greater than 3-sigma) exhibit inconsistent deformation behavior within a lot then they are outside the APC tuning range.

Figure 11:
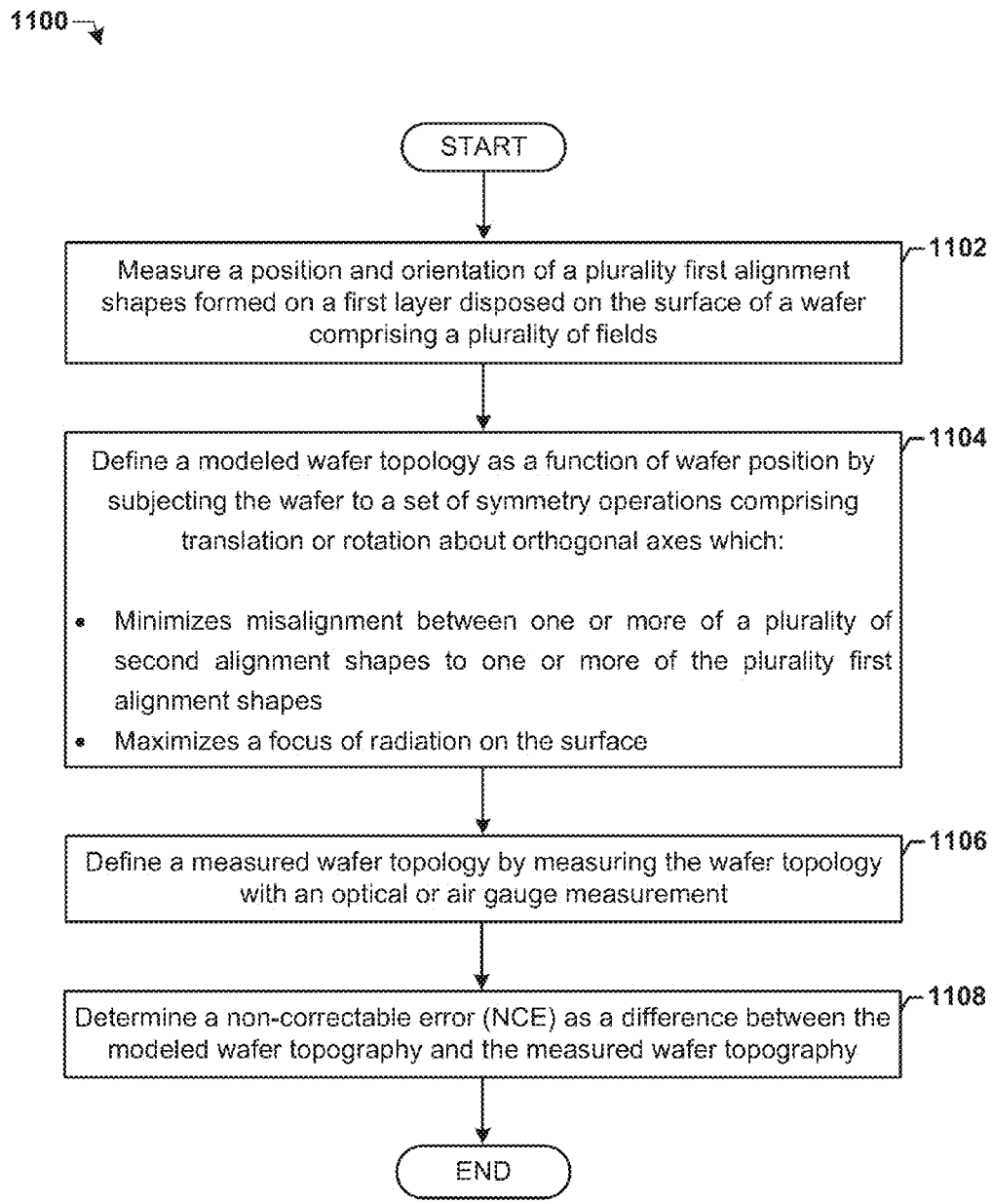
FIG. 11 illustrates some embodiments of a method of monitoring wafer topography.

FIG. 11 illustrates some embodiments of a method 1100 of monitoring wafer topography. While the method 1100 is illustrated and subsequently method 1200 are described as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

At 1102 a position and orientation of a plurality first alignment shapes are measured. The alignment shapes are formed on a first layer disposed on the surface of a wafer comprising a plurality of fields.

At 1104 a modeled wafer topography is defined as a function of wafer position by subjecting the wafer to a set of symmetry operations comprising translation or rotation about orthogonal axes which: (1) minimizes misalignment between one or more of a plurality of second alignment shapes formed on a patterning apparatus to one or more of the plurality of first alignment shapes, and (2) simultaneously maximizes a focus of radiation on the surface, wherein the radiation is provided by an exposure tool and filtered by the patterning apparatus. In some embodiments, the modeled wafer topography is determined by aligning a first subset of the plurality of first alignment shapes residing within a field with second subset of the plurality of second alignment which align to the first subset by subjecting the wafer to the first set of symmetry operations, and defining the modeled wafer topography from the first set of symmetry operations as a function of wafer position.

At 1106 a measured wafer topography is defined. In some embodiments, the measured wafer topography is determined by discharging a gas locally onto the wafer surface, monitoring a variation in a pressure of the gas as a function of position on a surface of the wafer, determining a height of the wafer surface as a function of the pressure. In some embodiments, the measured wafer topography is determined by emitting a focused incident beam of radiation to the wafer surface, reflecting the incident beam of radiation off the wafer surface resulting in a reflected beam of radiation, and determining a height of the wafer surface as a function of position from incident and reflected beams.

At 1108 a non-correctable error (NCE) is determined as a difference between the modeled wafer topography and the measured wafer topography.

Figure 12:
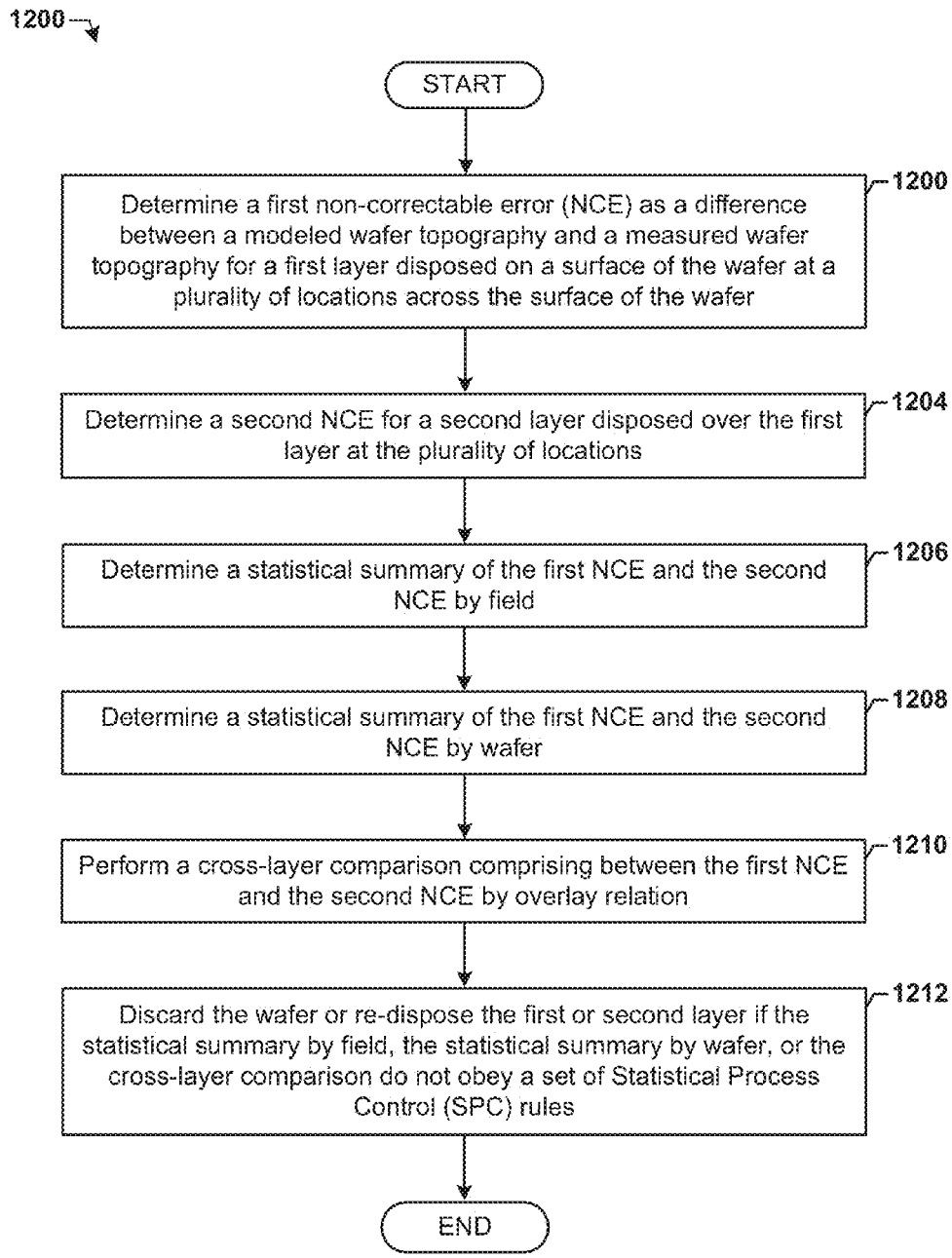
FIG. 12 illustrates some embodiments of a method of screening a wafer comprising a plurality of fields.

FIG. 12 illustrates some embodiments of a method of screening a wafer comprising a plurality of fields.

At 1202 a first non-correctable error (NCE) is determined as a difference between a modeled wafer topography and a measured wafer topography for a first layer disposed on a surface of the wafer at a plurality of locations across the surface of the wafer.

At 1204 a second NCE is determined for a second layer disposed over the first layer at the plurality of locations.

At 1206 a statistical summary of the first NCE and the second NCE are determined by field.

At 1208 a statistical summary of the first NCE and the second NCE are determined by wafer.

At 1210 a cross-layer comparison is performed comprising between the first NCE and the second NCE by overlay relation.

At 1212 the wafer discarded or the first or second layer are re-disposed if the statistical summary by field, the statistical summary by wafer, or the cross-layer comparison fail to meet criteria set forth by a set of SPC rules.

FIGS. 13A-13D illustrate some embodiments SPC rules applied to a statistical summary of NCEs.

Figure 13A:
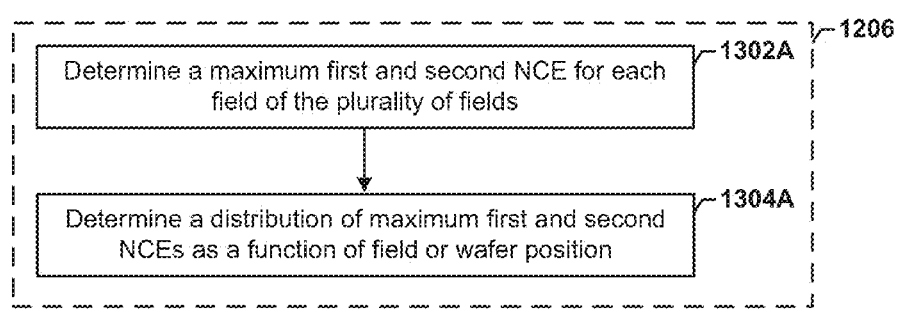
FIGS. 13A-13D illustrate some embodiments SPC rules applied to a statistical summary of NCEs.

FIG. 13A illustrates some embodiments of a first method 1300A for determining a statistical summary of the first NCE and the second NCE by field at 1206 in the embodiments of FIG. 12, wherein a maximum first and second NCE for each field of the plurality of fields is determined at 1302A, and a distribution of maximum first and second NCEs as a function of field or wafer position is determined at 1304A.

Figure 13B:
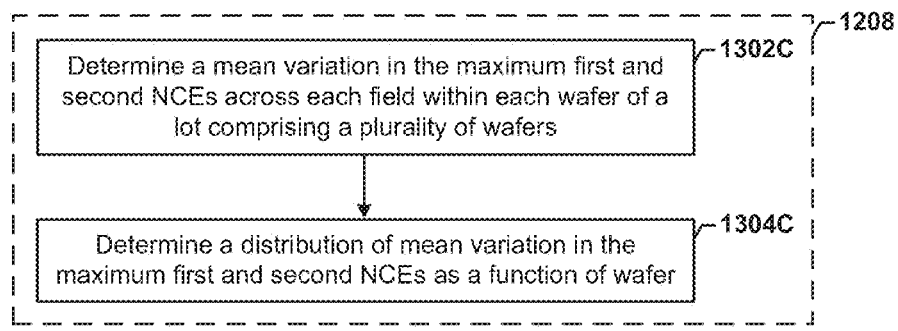

FIG. 13B illustrates some embodiments of a second method 1300B for determining a statistical summary of the first NCE and the second NCE by wafer at 1208 in the embodiments of FIG. 12, wherein a mean variation in the maximum first and second NCEs across each field within each wafer of a lot comprising a plurality of wafers is determined at 1302C, and a distribution of mean variation in the maximum first and second NCEs as a function of wafer is determined at 1304C.

Figure 13C:
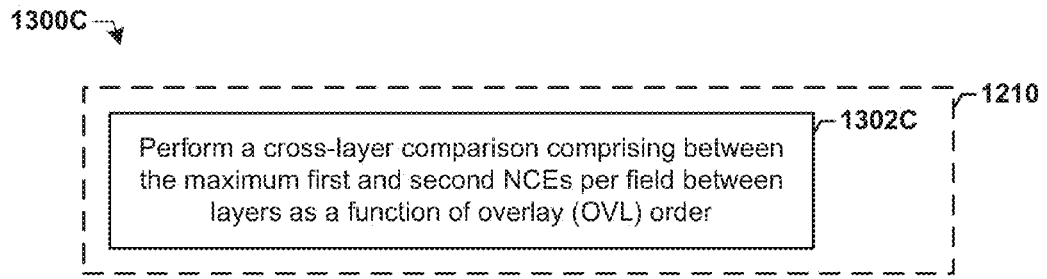

FIG. 13C illustrates some embodiments of a third method 1300C for performing a cross-layer comparison at 1210 in the embodiments of FIG. 12, wherein the cross-layer comparison is determined between the maximum first and second NCEs per field between layers as a function of OVL order at 1302C.

Figure 13D:
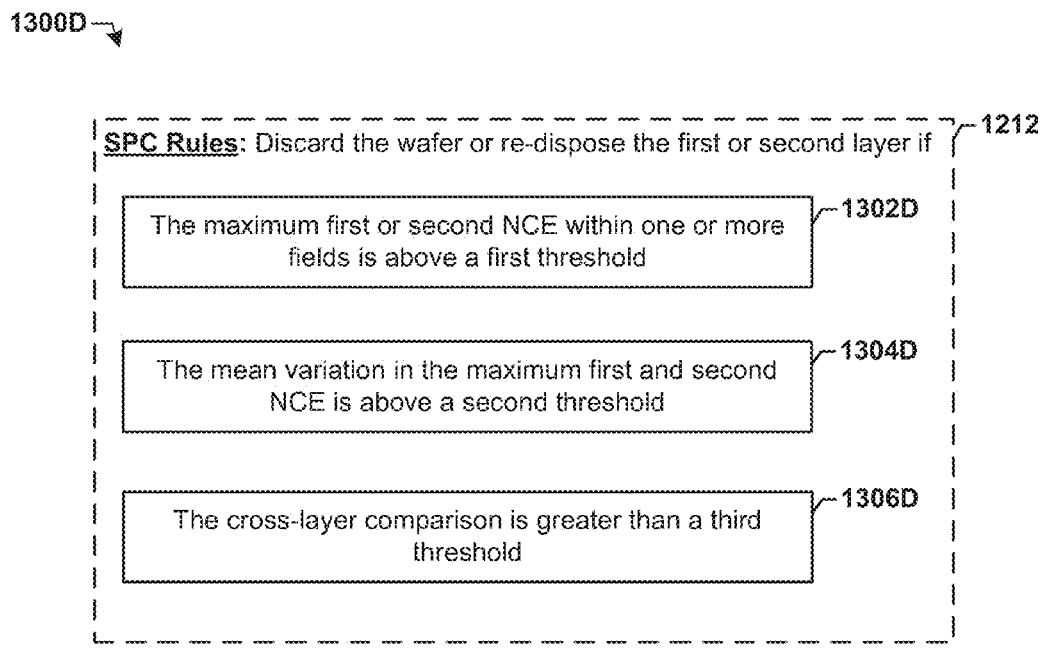

FIG. 13D illustrates some embodiments of first through third SPC rules 1302D-1306D which can be applied to the results of the first through third methods 1300A-1300C, respectively, which require discarding the wafer or re-disposing the first or second layer if: (1) the maximum first or second NCE within one or more fields is above a first threshold at 1302D, (2) the mean variation in the maximum first and second NCE is above a second threshold at 1304D, or (3) the cross-layer comparison is greater than a third threshold at 1306.

Therefore, it will be appreciated that some embodiments of the present disclosure relate to a method of monitoring wafer topography. A position and orientation of a plurality first alignment shapes are measured on a surface of a wafer. A modeled wafer topography as a function of wafer position is defined by subjecting the wafer an alignment which minimizes misalignment between the wafer and a patterning apparatus and maximizes a focus of radiation on the surface. A non-correctable error is determined as a difference between the modeled wafer topography and a measured wafer topography. A maximum non-correctable error per field is determined for a wafer, and a mean variation in the maximum non-correctable error across each field within each wafer of a lot is determined, both within a layer and across layers. These values are then verified against a set of statistical process control rules to determine if they are within a specification limit of the manufacturing process.

In some embodiments method of screening a wafer comprising a plurality of fields is disclosed, the method comprising determining a first non-correctable error as a difference between a modeled wafer topography and a measured wafer topography for a first layer disposed on a surface of the wafer at a plurality of locations across the surface of the wafer, determining a maximum first non-correctable error for each field of the plurality of fields, and discarding the wafer or re-disposing the first layer if the maximum first non-correctable error within one or more fields is above a first threshold.

In some embodiments a method of monitoring wafer topography is disclosed. The method comprises measuring a position and orientation of a plurality first alignment shapes formed on a first layer disposed on the surface of a wafer comprising a plurality of fields, defining a modeled wafer topography as a function of wafer position by subjecting the wafer to a set of symmetry operations comprising translation or rotation about orthogonal axes which: minimizes misalignment between one or more of a plurality of second alignment shapes formed on a patterning apparatus to one or more of the plurality of first alignment shapes, and simultaneously maximizes a focus of radiation on the surface, wherein the radiation is provided by an exposure tool and filtered by the patterning apparatus. A measured wafer topography is then defined, and a non-correctable error is determined as a difference between the modeled wafer topography and the measured wafer topography.

In some embodiments a metrology system is disclosed, comprising an alignment stage configured to position a wafer relative to an exposure tool by subjecting the wafer to a set of symmetry operations comprising translation or rotation about orthogonal axes, a surface measurement tool configured create a measured wafer map by measuring a surface topography of the wafer as a function of wafer position, and a scanning tool configured to determine second locations of a plurality of second alignment shapes formed on a patterning apparatus relative first locations of a plurality of first alignment shapes disposed on a surface of the wafer, and to direct a controller to position the alignment stage based upon the first and second locations, and a computation unit configured to create a modeled wafer map based upon the set of symmetry operations as a function of wafer position, and to determine a first non-correctable error as a difference between a modeled wafer topography and a measured wafer topography.

Although the disclosure has been shown and described with respect to a certain aspect or various aspects, equivalent alterations and modifications will occur to others of ordinary skill in the art upon reading and understanding this specification and the annexed drawings. In particular regard to the various functions performed by the above described components (assemblies, devices, circuits, etc.), the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the disclosure. In addition, while a particular feature of the disclosure may have been disclosed with respect to only one of several aspects of the disclosure, such feature may be combined with one or more other features of the other aspects as may be desired and advantageous for any given or particular application. Furthermore, to the extent that the terms "including", "includes", "having", "has", "with", or variants thereof are used in either the detailed description and the claims, such terms are intended to be inclusive in a manner similar to the term "comprising".

What is claimed is:

1. A method of screening a wafer with a plurality of reticle fields, the method comprising:
    modeling a topography over a surface of the wafer based on a plurality of first alignment shapes in a first layer overlying the surface to generate a modeled topography for the first layer, wherein the plurality of first alignment shapes is spaced over the surface with a first resolution;
    measuring the topography with a second resolution greater than the first resolution to generate a measured topography for the first layer;
    determining a plurality of first non-correctable errors for the first layer as a difference between the modeled topography and the measured topography, wherein the plurality of first non-correctable error are determined at a plurality of locations across the surface of the wafer;
    determining a maximum first non-correctable error from the plurality of first non-correctable errors for each reticle field of the plurality of reticle fields; and
    discarding the wafer or re-disposing the first layer if the maximum first non-correctable error within one or more reticle fields is above a first threshold.

2. The method of claim 1, further comprising:
    determining a mean variation of the maximum first non-correctable errors of the plurality of reticle fields; and
    discarding the wafer or re-disposing the first layer on the wafer if the mean variation is above a second threshold.

3. The method of claim 2, further comprising:
    determining a second non-correctable error for a second layer disposed over the first layer at the plurality of locations;
    performing a cross-layer comparison based on a difference between the first non-correctable error and the second non-correctable error at a location; and
    discarding the wafer or re-disposing the second layer if a result of the cross-layer comparison is greater than a third threshold.

4. The method of claim 3, wherein a second alignment shape formed on the second layer is aligned to a first alignment shape formed on the first layer when patterning the second layer.

5. The method of claim 1, further comprising:
    locating the plurality of first alignment shapes with a scanning tool; and
    aligning the plurality of first alignment shapes with a plurality of second alignment shapes formed on a patterning apparatus by subjecting the wafer to a first set of symmetry operations comprising translation or rotation about orthogonal axes which minimizes aggregate misalignment between the plurality of first alignment shapes and the plurality of second alignment shapes.

6. The method of claim 5, wherein the modeled topography is determined by:
    aligning a first subset of the plurality of first alignment shapes residing within a field with a second subset of the plurality of second alignment shapes which align to the first subset by subjecting the wafer to the first set of symmetry operations which minimizes aggregate misalignment between the first and second subsets; and
    defining the modeled topography from the first set of symmetry operations as a function of wafer position.

7. The method of claim 6, further comprising:
    aligning the first subset of the plurality of first alignment shapes with the second subset of the plurality of second alignment shapes by subjecting the wafer to a second set of symmetry operations comprising translation or rotation about orthogonal axes as a function of position within the field.

8. The method of claim 1, wherein the measured topography is determined by:
    discharging a gas locally towards the surface of the wafer;
    monitoring a variation in a pressure of the gas as a function of position on the surface of the wafer; and
    determining a height of the first layer as a function of the pressure.

9. The method of claim 1, wherein the measured topography is determined by:
    emitting a focused incident beam of radiation towards an upper surface of the first layer, wherein the incident beam of radiation forms a first angle with a normal vector to the upper surface of the first layer;
    reflecting the incident beam of radiation off the upper surface of the first layer, resulting in a reflected beam of radiation, wherein the reflected beam of radiation forms a second angle with the normal vector to the upper surface of the first layer; and
    determining a height of the upper surface of the first layer as a function of position from the first angle or the second angle.

10. A method of monitoring topography over a wafer, said method comprising:
    measuring a position and orientation of a plurality of first alignment shapes formed on a first layer disposed on a surface of a wafer comprising a plurality of fields, wherein the plurality of first alignment shapes are spaced over the surface of the wafer with a first resolution;
    defining a modeled topography of a topography over the surface of the wafer as a function of wafer position by subjecting the wafer to a set of symmetry operations comprising translation or rotation about orthogonal axes which:
        minimizes misalignment of one or more of a plurality of second alignment shapes formed on a patterning apparatus to one or more of the plurality of first alignment shapes; and
        maximizes a focus of radiation on the surface, wherein the radiation is provided by an exposure tool and filtered by the patterning apparatus;
    defining a measured topography by measuring the topography over the surface of the wafer without recognizing the plurality of first alignment shapes, and with a second resolution greater than the first resolution; and
    determining a first non-correctable error as a difference between the modeled topography and the measured topography.

11. The method of claim 10, further comprising:
    determining a maximum first non-correctable error for each field of the plurality of fields;
    determining a mean variation of the maximum first non-correctable errors of the plurality of fields; and
    discarding the wafer or re-disposing the first layer on the wafer if the maximum first non-correctable error within one or more fields is above a first threshold or if the mean variation within a wafer is above a second threshold.

12. The method of claim 11, further comprising:
    determining a maximum second non-correctable error for a second layer disposed over the first layer, wherein a second alignment shape formed on the second layer is aligned to a first alignment shape formed on the first layer when patterning the second layer;

performing a cross-layer comparison based on a difference between the maximum first non-correctable error and the maximum second non-correctable error at a field; and discarding the wafer or re-disposing the second layer if a result of the cross-layer comparison is greater than a third threshold.

13. The method of claim 12, wherein the maximum first non-correctable error, the second non-correctable error, the mean variation, or the result of the cross-layer comparison are sorted by tool location within an in-line fabrication structure comprising a plurality of tools.

14. The method of claim 12, wherein the first or second layers comprise a poly-silicon layer, a replacement metal gate layer, an oxide layer, a dielectric layer, a contact layer, a via layer, or a metallization layer.

15. A metrology system, comprising:
an alignment stage configured to position a wafer relative to an exposure tool by subjecting the wafer to a set of symmetry operations comprising translation or rotation about orthogonal axes;
a surface measurement tool configured to create a measured map by measuring a surface topography over the wafer as a function of wafer position and with a first resolution;
a scanning tool configured to determine first locations of a plurality of first alignment shapes disposed over a surface of the wafer relative to second locations of a plurality of second alignment shapes formed on a patterning apparatus relative, and to direct a controller to position the alignment stage based upon the first and second locations, wherein the plurality of first and second alignment shapes are spaced with a second resolution less than the first resolution; and
a computation unit configured to create a modeled map of the surface topography based upon the set of symmetry operations as a function of wafer position, and to determine a first non-correctable error as a difference between a modeled wafer topography and a measured wafer topography.

16. The metrology system of claim 15, wherein the wafer comprises a plurality of fields with each field comprising a plurality of the plurality of first alignment shapes formed on a first layer, and the computation unit is further configured to determine a maximum first non-correctable error for each field.

17. The metrology system of claim 16, wherein the computation unit is further configured to:
determine a mean variation of the maximum first non-correctable errors for the plurality of fields; and
compare the mean variation with another mean variation of another wafer of a lot of wafers comprising the wafer.

18. The metrology system of claim 17, wherein the computation unit is further configured to:
determine a second non-correctable error for a second layer disposed over the first layer; and
perform a cross-layer comparison based on a difference between the first non-correctable error and the second non-correctable error at a location.

19. The metrology system of claim 18, wherein the computation unit is further configured to determine that the wafer is unacceptable for a manufacturing process if the maximum first non-correctable error, the mean variation, or a result of the cross-layer comparison is not within one or more ranges or less than one or more thresholds predetermined for the manufacturing process.

20. The metrology system of claim 16, wherein the surface measurement tool further comprises:
an air gauge configured to discharge a gas locally toward the surface of the wafer, the air gauge further comprising a sensor configured to detect a variation in a pressure of the gas as a function of position and configured to determine a height of the first layer as a function of the variation in pressure; or
an optical tool configured to emit a focused incident beam of radiation towards an upper surface of the first layer, receive a reflected beam of radiation from the upper surface of the first layer, and to determine a height of the first layer as a function of position from the incident and reflected beams of radiation.

* * * * *